United States Patent [19]

Hershberger et al.

[11] Patent Number: 4,637,981
[45] Date of Patent: Jan. 20, 1987

[54] ANTIBIOTIC A-4696 FACTOR G

[75] Inventors: Charles L. Hershberger, New Palestine; Kurt E. Merkel, Mooresville; Robert E. Weeks; Gene M. Wild, both of Indianapolis, all of Ind.

[73] Assignee: Eli Lilly and Company, Indianapolis, Ind.

[21] Appl. No.: 593,015

[22] Filed: Mar. 26, 1984

Related U.S. Application Data

[60] Division of Ser. No. 426,493, Sep. 29, 1982, Pat. No. 4,461,723, which is a continuation-in-part of Ser. No. 217,960, Dec. 18, 1980, abandoned.

[51] Int. Cl.$^4$ .................. C12P 19/60; C12P 19/56; C12N 1/20; C12R 1/045
[52] U.S. Cl. .................................. 435/75; 435/78; 435/827; 435/253
[58] Field of Search .............. 435/75, 78, 827, 253; 260/112.5 R; 424/118; 530/322

[56] References Cited

U.S. PATENT DOCUMENTS

| | | | |
|---|---|---|---|
| 3,928,571 | 12/1975 | Raun | 424/118 |
| 3,952,095 | 4/1976 | Hamill et al. | 424/118 |
| 4,064,233 | 12/1977 | Hamill et al. | 424/118 |
| 4,115,552 | 9/1978 | Hamill et al. | 424/118 |
| 4,375,513 | 3/1983 | Debono et al. | 435/827 |
| 4,461,723 | 7/1984 | Hershberger et al. | 260/112.5 R |

Primary Examiner—Thomas G. Wiseman
Assistant Examiner—John E. Tarcza
Attorney, Agent, or Firm—William B. Scanlon

[57] ABSTRACT

Glycopeptide antibiotic A-4696G is produced by culturing *Actinoplanes missouriensis* mutant strain ATCC 31681 under submerged aerobic fermentation conditions, and is recovered from the fermentation broth by resin adsorption and chromatographic purification. A-4696G inhibits the growth of bacteria pathogenic to man and animals and also enhances the growth of ruminants by increasing feed utilization.

2 Claims, 1 Drawing Figure

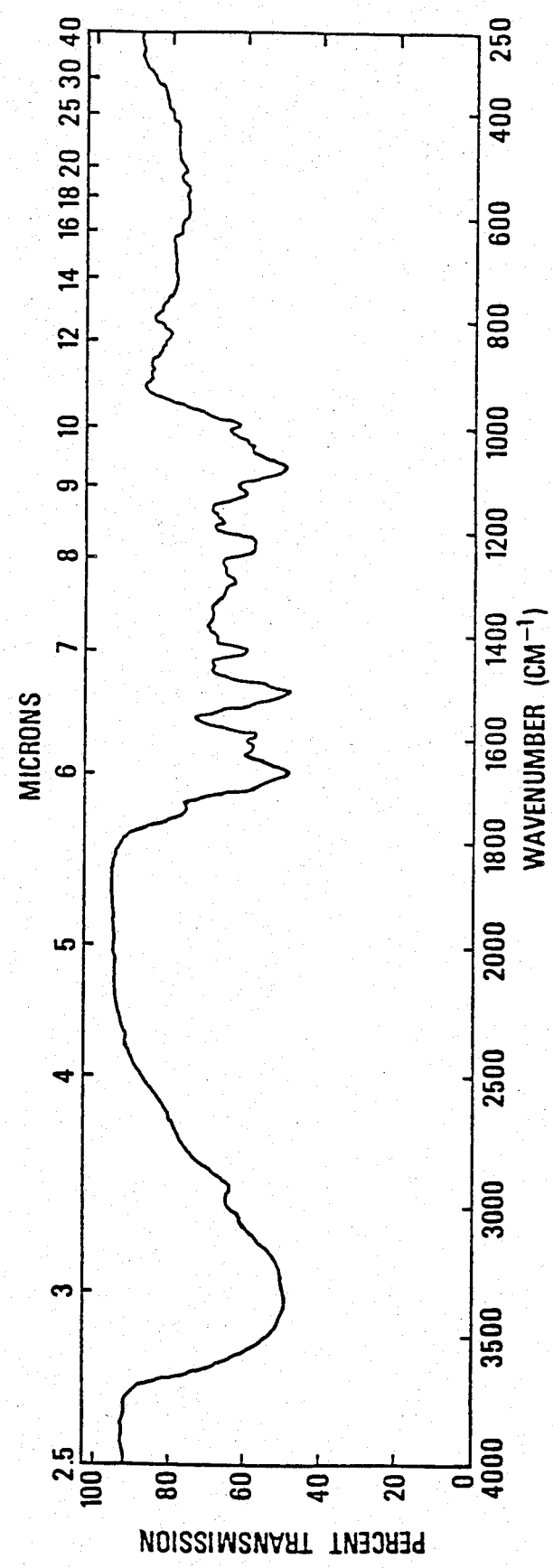

ANTIBIOTIC A-4696 FACTOR G

CROSS-REFERENCE TO RELATED APPLICATION

This application is a division of application Ser. No. 426,493 filed Sept. 29, 1982, now U.S. Pat. No. 4,461,723 issued July 24, 1984 as a continuation-in-part of application Ser. No. 217,960 filed Dec. 18, 1980, now abandoned.

SUMMARY OF THE INVENTION

This invention relates to a novel antibiotic and to its preparation. This antibiotic, which is a new member of the A-4696 antibiotic complex, has been designated A-4696 factor G or A-4696G.

A-4696G is a glycopeptide antibiotic produced by culturing an A-4696G-producing strain of *Actinoplanes missouriensis,* such as ATCC 31681, in an aqueous nutrient medium under submerged aerobic fermentation conditions.

The antibiotic is recovered from the crude fermentation broth by adsorption on resins and is purified by chromatography.

A-4696G is a basic substance forming acid addition salts which are also part of this invention. Pharmaceutically acceptable acid addition salts of A-4696G are especially useful compounds of this invention. The term "A-4696G compound" as used herein refers to A-4696 factor G or a pharmaceutically acceptable salt of A-4696 factor G.

A-4696G inhibits the growth of organisms which are pathogenic to man and animals. More specifically, A-4696G is an antibacterial agent which is especially useful against gram-positive bacteria. In addition, A-4696G is useful as a growth promotion agent for animals.

BACKGROUND OF THE INVENTION

Many antibiotic-producing microorganisms are known to produce more than one antibiotic substance during fermentation. Some produce a complex of antibiotic substances which are similar in structure to one another or which differ structurally. One such microorganism is Actinoplanes sp. ATCC 23342 which produces antibiotic A-4696, U.S. Pat. No. 3,952,095. Antibiotic A-4696 factors A and B were subsequently discovered in the A-4696 complex and are described by U.S. Pat. No. 4,115,522.

The separation of individual antibiotic substances from an antibiotic complex containing multi-factors often presents problems, particularly when a single factor is desired for commercial use. Approaches to obtain a single factor include strain selection and mutation of the microorganism in the hope that the new strain will provide the single factor or more abundant quantities of the desired factor. Oftentimes in the pursuit of this approach, a new strain is found which produces a new antibiotic compound either alone or along with the factors produced by the prior strain.

The present invention provides a new A-4696 factor which is obtained by culturing a new strain of *Actinoplanes missouriensis,* the organism known to produce antibiotic A-4696 complex and the individual A and B factors.

The present invention arose out of development work involving strain selection, strain mutation, and isolation efforts directed at the A-4696 antibiotic. Other novel A-4696 factors discovered by Manuel Debono, Kurt E. Merkel, Robert E. Weeks and Herald J. Cole are described in U.S. Pat. No. 4,322,406.

DESCRIPTION OF THE DRAWING

The infrared absorption spectrum of A-4696 factor G dihydrochloride in KBr pellet is presented in the accompanying drawing.

DETAILED DESCRIPTION

The following paragraphs describe the properties of the new antibiotic of this invention, A-4696 factor G.

A-4696G, as the dihydrochloride salt, is a white crystalline compound. Elemental analysis of A-4696G dihydrochloride salt indicates that it has the following approximate percentage composition: carbon, 52.90%; hydrogen, 4.29%; nitrogen, 6.39%; oxygen, 30.96% (by difference); chlorine, 5.46%. A-4696G has an approximate molecular weight of about 1700.

The infrared absorption spectrum of A-4696G (as the dihydrochloride salt) in KBr pellet is shown in the accompanying drawing. Significant absorption maxima occur at the following frequencies ($cm^{-1}$): 3384 (broad), 2924 (weak), 1730 (shoulder), 1659 (intense), 1616 (weak), 1590 (weak), 1504 (intense), 1488 (shoulder), 1427 (medium), 1289 (weak), 1226 (doublet), 1214 (doublet), 1179 (weak), 1119 (weak), 1060 (intense), 1028 (weak), 1015 (shoulder), 986 (weak), 899 (very weak), 881 (very weak), 815 (weak), 801 (shoulder), 769 (shoulder), 751 (shoulder) and 711 (weak).

Electrometric titration of A-4696G in 66% aqueous dimethylformamide (initial pH 7.89) results in a gradual amount of titrant being consumed between pH 3.5 and 13.5.

The ultraviolet absorption spectrum of A-4696G dihydrochloride in water gives an absorption maximum of 279 nm ($E_{1\ cm}^{1\%} = 53$).

A-4696G dihydrochloride is soluble in water, but is insoluble in solvents such as methanol, acetone, diethyl ether, chloroform, benzene, and the like.

In addition to the free base and hydrochloride salt forms of A-4696G, other acid addition salts of A-4696G are also part of this invention. Representative and suitable salts of A-4696G include those salts formed by standard reactions with both organic and inorganic acids such as, for example, sulfuric, hydrochloric, phosphoric, methanesulfonic, benzenesulfonic, picric, and like acids.

Pharmaceutically acceptable acid addition salts such as the hydrochloride and sulfate salts are an especially preferred group of salts of this invention. "Pharmaceutically acceptable" salts are salts which are not unduly toxic as a whole toward warm-blooded animals.

The A-4696 factor G, like the A-4696 complex and its individual factors, undergoes hydrolysis over about 70 minutes in refluxing 5% hydrochloric acid to form the pseudo-aglycone represented by the following structural formula.

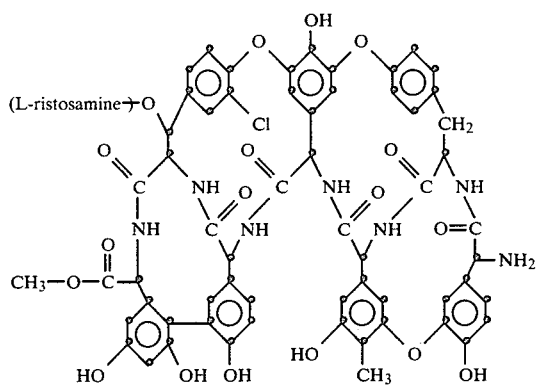

The pseudo-aglycone is described by Manuel Debono in U.S. Pat. No. 4,322,343. The pseudo-aglycone precipitates from the hydrolysis mixture.

As is shown in the above formula, the pseudo-aglycone contains six phenolic hydroxy groups and a free amino group in addition to the amino function in the attached amino sugar, ristosamine. As with the other A-4696 factors, factor G of this invention contains neutral sugars bonded to the pseudo-aglycone nucleus at one or more of the phenolic groups. Factor G differs from the other A-4696 factors in the type and number of neutral sugars attached to the nucleus and also in the point of attachment.

The structural formula for factor G depicted below was determined by a study of its nuclear magnetic resonance spectra (360 MHz) and its other spectral and chemical properties.

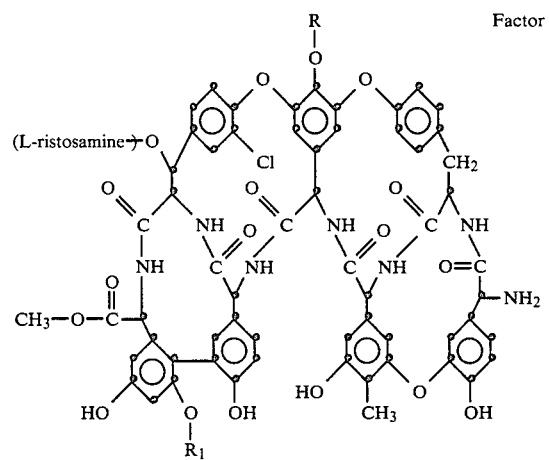

Factor G

In the above formula R is

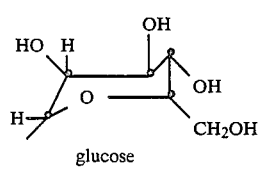

glucose and $R_1$ is

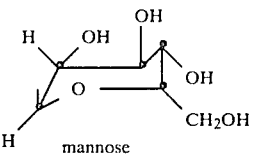

mannose

The L-ristosamine has the following structure

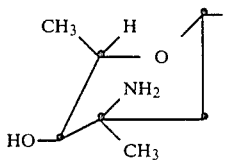

Factor G is distinguishable from the known factor A as well as the factors described in U.S. Pat. No. 4,322,406, by its retention on high performance liquid chromatography (HPLC). Below are listed the retention values (K'-value) for several A-4696 factors using $C_{18}$ reverse phase HPLC (Waters Assoc. μBondapak $C_{18}$) at ambient temperature and 2% aq. acetic acid-:acetonitrile (90:10, v:v) and 2% aq. acetic acid:acetonitrile (70:30, v:v) as the solvents.

| A-4696 Factor | K'-Value |
|---|---|
| A | 1.60 |
| $B_1$ | 1.99 |
| $B_2$ | 3.84 |
| $B_3$ | 2.50 |
| $C_{1a}$ | 2.92 |
| $C_3$ | 4.23 |
| $E_1$ | 0.38 |
| G | 4.42 |

THE MICROORGANISM

The new microorganism of this invention was obtained by a series of nitrosoguanidine mutations from a strain of *Actinoplanes missouriensis* ATCC 23342, the strain which produces the A-4696 complex described in U.S. Pat. No. 3,952,095. The new microorganism produces factor G as a major factor in amounts corresponding to about 30% of the total activity. Other A-4696 factors are coproduced.

For characterization purposes, the new micro-organism was compared with the parent culture ATCC 23342. Both cultures produce similar substrate or primary mycelia. Neither aerial nor secondary mycelia were observed. No sporangia were observed. Thirteen agar-plating media, as well as Liquidambar, Pinus, and Passiflora pollen, were used in an attempt to induce sporangia formation. None was observed either with a light microscope or scanning electron microscope.

Sporangia were observed in culture ATCC 23342 earlier by Dr. John N. Couch, University of North Carolina. They were described as rather small, 4–11 μM, subglobose, rarely globose, usually with an irregular wall, i.e., in sectional view the wall was irregularly wavy.

Mature spores were arranged in one or more indistinct coils in the sporangium. Sporangial dehiscence is by the swelling of an intersporal substance which causes the sporangium to enlarge and assume an almost smooth spherical shape. Spores were motile, about 1–1.5 μM in diameter, globose to subglobose.

Culture ATCC 23342 has a Type II cell wall, both meso-2,6-diaminopimelic acid and hydroxydiaminopimelic acid being detected in the cell wall [see Becker, B. et al., "Rapid Differentiation between Norcardia and Streptomyces by Paper Chromatography of Whole Cell Hydrolysates", *Appl. Microbiol.* 11: 421–423 (1964)].

Culture ATCC 23342 and culture ATCC 31681 differ mainly in the pigmentation of the primary mycelia. Culture ATCC 23342 has an orange-colored mycelium, ranging from moderate to brownish orange to strong orange yellow, depending on the medium. Culture ATCC 31681 has no distinct color. A yellowish gray best describes the mycelium. No characteristic soluble pigments were produced by culture ATCC 31681.

Culture ATCC 23342 produces a reddish-brown soluble pigment on ISP #7 and tomato paste-oatmeal (TPO) agar media.

Melibiose is utilized by ATCC 23342 but not ATCC 31681. A summary of the similarities and differences between ATCC 23342 and ATCC 31681 is given in Table 1.

TABLE 1
Comparison of ATCC 31681 and ATCC 23342 Characteristics

| Similarities | Differences |
|---|---|
| Antibiotic sensitivity | Carbon utilization |
| Biosynthesis of A-4696 factors | Color of mycelium |
| Catalase positive | Degree of gelatin liquefaction |
| Growth on agar-slant media | |
| Lack of aerial mycelia | Degree of growth-ring formation in milk |
| Lack of chromogenicity | |
| Lack of sporangia | Degree of starch hydrolysis |
| NaCl tolerance | Growth in selected vegetative media |
| Nitrate reduction: negative | |
| Optimum growth on Bennett' agar | Growth characteristics on ISP #7 and calcium maleate agar |
| pH range of growth | |
| Phosphatase: positive | |
| Skim milk: negative | Soluble pigment |
| Sucrose tolerance | A-4696 factor production |
| Temperature range | |
| Urease: positive | |

Methods

The methods recommended for the International Streptomyces Project (ISP) for the characterization of Streptomyces species have been followed (see E. B. Shirling, and D. Gottlieg, "Methods of Characterization of Streptomyces Species. *Internal. Journal of Systematic Bacteriology*, 16 (3):313–340 (1966)], along with certain supplementary tests.

Carbon utilization was determined on ISP #9 basal medium to which filter-sterilized carbon sources were added to equal a final concentration of 1.0%. Plates were incubated at 30° C. and read after 14 days.

Melanoid pigment production (chromogenicity) was determined with ISP #1 (tryptone-yeast extract broth). Neither culture grew after 7 days incubation on ISP #6 (peptone-yeast extract-iron agar) or ISP #7 (tyrosine agar).

Starch hydrolysis was determined by testing for the presence of starch with iodine on ISP #4 (inorganic salts-starch agar) plates.

Temperature range, NaCl and sucrose tolerance, pH range, and antibiotic sensitivity were determined using ISP #2 (yeast-malt extract agar) plates. Plates were incubated at 30° C. for 14 days. The temperatures tested were 5°, 10°, 15°, 20°, 25°, 30°, 37°, 40°, 45°, 50° and 55° C.

NaCl tolerance was measured by adding NaCl to the agar to equal: 0, 2, 4, 6, 8, 10 and 12%. Sucrose tolerance was measured by adding sucrose to equal: 0, 2, 4, 6, 8, 10, 12, 15 and 20%. The pH range was determined using the following buffers at a concentration of 0.05M; citric acid, pH 3, 4, 5; 2-(N-morpholino)ethanesulfonic acid, pH 6; 3-(N-morpholino)propanesulfonic acid, pH 7; N-tris(hydroxymethyl)methylglycine, pH 8; 2-(cyclohexylamino)ethanesulfonic acid, pH 8.5, 9.0, 9.5; 3-cyclohexylamino-1,1-propanesulfonic acid, pH 10, 11. The pH of the agar after 14 days incubation was taken as the correct value since some of the buffers failed to hold their adjusted pH. Buffer toxicity was tested by adjusting all the buffers to pH 7.0 and determining growth. Culture ATCC 23342 was sensitive to citric acid.

The methods of Blazevic and Ederer were followed for the enzyme assays (D. J. Blazevic and G. M. Ederer, "Principles of Biochemical Tests in Diagnostic Microbiology," John Wiley and Sons, New York, N.Y., 1975). Color names were assigned using ISCC-NBC Centroid Color Charts, standard sample No. 2106 [see K. L. Kelly and D. B. Judd, The ISCC-NBS Centroid Color Charts Standard Sample No. 2106, U.S. Dept. of Commerce, National Bureau of Standards, Washington, D.C. 20234].

Antibiotic sensitivity was determined using sensitivity discs padded on the surface of seeded agar plates. The following antibiotics were used: Cephalothin (sodium) 30 μg., Erythromycin (estolate) 15 μg., Gentamicin 10 μg., Lincomycin 2 μg., Nalidixic acid 30 μg., Penicillin 10 μg. Polymixin G 300 units, Streptomycin 10 μg., Tetracycline 30 μg., Vancomycin HCl 30 μg. Both cultures ATCC 23342 and ATCC 31681 were sensitive to all the antibiotics tested.

The cultural characteristics of the ATCC 23343 and ATCC 31681 cultures are compared in Table 2.

TABLE 2

| Agar[2] | | Cultural Characteristics[1] | |
|---|---|---|---|
| | | ATCC 23342 | ATCC 31681 |
| ISP #2 | G | good | poor |
| | R | 53. moderate orange | 93. yellowish gray |
| | Am | none | none |
| | SP | none | none |
| ISP #3 | G | poor | poor |
| | R | 76. light yellowish brown | 93. yellowish gray |
| | Am | none | none |
| | SP | none | none |
| ISP #4 | G | abundant | fair |
| | R | 50. strong orange | 93. yellowish gray |
| | Am | none | none |
| | SP | none | none |
| ISP #5 | G | fair | good |
| | R | 68. strong orange | 93. yellowish gray |
| | Am | none | none |
| | SP | none | none |
| ISP #7 | G | poor | none |
| | R | 54. brownish orange | none |
| | Am | none | none |
| | SP | reddish-brown | none |
| Bennett's | G | abundant | good |
| | R | 53. moderate orange | 93. yellowish gray |
| | Am | none | none (moist surface) |
| | SP | none | none |
| Calcium malate | G | good | none |
| | R | 50. strong orange (shiny) | none |
| | Am | none | none |
| | SP | none | none |
| Czapek's | G | good | fair |
| | R | 71. moderate orange yellow | 93. yellowish gray |

TABLE 2-continued

| | | Cultural Characteristics[1] | |
|---|---|---|---|
| Agar[2] | | ATCC 23342 | ATCC 31681 |
| | Am | none | none |
| | SP | none | none |
| Glucose | G | good | fair |
| asparagine | R | 71. moderate orange yellow | 93. yellowish gray |
| | Am | none | none |
| | SP | none | none |
| TPO | G | good | poor |
| | R | 55. strong brown | 93. yellowish gray |
| | Am | none | none |
| | SP | faint reddish-brown | none |
| Anio- | G | poor | fair |
| Hensens | R | 70. light orange yellow | 93. yellowish gray |
| | Am | none | none |
| | SP | none | none |
| 53H | G | fair | fair |
| medium | R | 54. brownish orange | 79. l. gy. yellowish brown |
| | Am | none | none |
| | SP | none | none |
| Czapek's | G | abundant | abundant |
| peptone | R | 54. brownish orange | 90. grayish yellow |
| | Am | none | none |
| | SP | none | none |

[1]G = growth; R = reverse or underside of colony;
Am = aerial mycelium; SP = soluble pigment
Numbers in the TABLE are color chart numbers of ISCC-NBC Centroid Color Charts
[2]ISP = International Streptomyces Project agars
TPO = Tomato paste-oatmeal agar
53H medium has the following composition:

| Yeast extract | 2 g. |
|---|---|
| CaCo$_3$ | 3 g. |
| Na$_2$S$_2$O$_3$.5H$_2$O | 0.5 g. |
| V$_8$ juice | 200 ml. |
| Agar | 20 g. |
| Deionized water | 800 ml. |

In Tables 3 and 4 which follow, carbon utilization (Table 3) and miscellaneous physiological characteristics (Table 4) are compared.

TABLE 3

| | Carbon Utilization | |
|---|---|---|
| Carbon Source | ATCC 23342 | ATCC 31681 |
| Control - no carbon | − | − |
| D-Glucose | ++ | + |
| L-Arabinose | ++ | + |
| Cellobiose | ++ | + |
| D-Fructose | ++ | + |
| D-Galactose | ++ | (+) |
| i-Inositol | − | − |
| D-Mannitol | ++ | + |
| Melibiose | + | − |
| Raffinose | − | − |
| D-Rhamnose | ++ | (+) |
| D-Ribose | − | − |
| Salicin | + | (+) |
| Sucrose | ++ | + |
| D-Xylose | ++ | + |

++ = equal to or > glucose control, positive utilization
+ = < glucose control, > no carbon control, positive utilization
(+) = growth questionable, doubtful utilization
− = no growth, negative utilization

TABLE 4

| Additional Physiological Characteristics | | |
|---|---|---|
| | ATCC 23342 | ATCC 31681 |
| ISP #1 (chromogenicity) | − | − |
| Catalase | + | + |
| Phosphatase | + (slow) | + (slow) |
| Urease | + (slow) | + (slow) |
| Temperature growth range | 15–37° C. | 15–37° C. |
| NaCl tolerance | <2% | <2% |
| Sucrose tolerance | 15% | 15% |

TABLE 4-continued

| Additional Physiological Characteristics | | |
|---|---|---|
| | ATCC 23342 | ATCC 31681 |
| Nitrite reduction | − | − |
| Starch hydrolysis | + (fair) | + (weak) |
| pH growth range | 6–7 | 6–7 |
| Skim milk: growth ring | + | − |
| Skim milk: reaction | − | − |
| Gelatin liquefaction | + (40%) | + (20%) |
| Soluble pigment | + | − |

The A-4696G producing strain of *Actinoplanes missouriensis*, ATCC 31681, is obtained as a pure culture free of other strains by culturing the microorganism on slants, agar plates and in sterile aqueous nutrient media. The new mutant strain is useful in the preparation of antibiotic A-4696G. Accordingly, a further aspect of this invention provides as a pure culture *Actinoplanes missouriensis* strain ATCC 31681 as described hereinabove.

The above described *Actinoplanes missouriensis* strain ATCC 31681 when cultured produces factor G and other antibiotic substances with factor G comprising about 30% of the total activity. The novel strain can be grown in a variety of culture media which contain assimilable sources of carbon, nitrogen and inorganic salts. Suitable carbon sources include, for example, the carbohydrates such as starch, glucose, dextrin, and the like. Glycerol can also be used as a carbon source by the microorganism. Molasses is a convenient and cheap source of carbohydrate; however, starch is preferred. Sources of nitrogen include the the amino acids, peptones and yeast. Nutrient oils such as soybean oil and peanut oil can also serve as nitrogen sources. Yeast, however, is a preferred source of nitrogen.

As is the case with other antibiotic-producing microorganisms, inorganic salts are incorporated in the culture medium. Inorganic salts which provide sodium, potassium, calcium, ammonium, phosphate, chloride, sulfate and like cations and anions can be used. Likewise, trace elements essential for the growth of microorganisms can be added to the culture medium either separately or along with other nutrients. Such trace amounts of essential elements usually occur in sufficient amounts as impurities in the other ingredients of the medium.

Sources of growth factors, such as distiller's solubles and yeast extracts, can be included in the factor G culture medium to enhance production of the antibiotic.

The new factor G-producing strain can be cultured over a wide pH range; however, for maximum production the pH of the culture medium is between about 6 and about 7.0 and preferably between about pH 6.5 to pH 7. During the growth of the microorganism the pH of the medium increases from the preferred range to a pH of about 7.0 to 7.5.

Small quantities of the antibiotic are obtained from shake flask size fermentations of from 250 ml. to 2,000 ml. in size. For large scale production of the antibiotic factor 25,000 gallon to 50,000 gallon fermentors are used. Submerged aerobic fermentation conditions are preferred for the large scale production of factor G. As with the large-scale production of other antibiotics the large sterile fermentor, charged with the culture medium, is inoculated with sufficient inoculum to achieve onset of growth in a reasonable time following inoculation. The inoculum for the large tanks is obtained as follows. First, growth of the microorganism on an agar slant is used to inoculate a shake flask containing the culture medium. The shake flask size culture is allowed to grow and the full grown vegetative medium is then transferred to a larger volume, a so-called bump medium, contained in a large bump tank of intermediate size. When growth in the bump tank has reached optimum, the contents of the tank are charged into the large scale fermentor.

The *A. missouriensis* ATCC 31681 can be grown in the fermentation medium at temperatures between about 20° C. and about 40° C. Preferred temperatures appear to be about 30° C. for maximum production of factor G.

During the fermentation of the new strain, sterile air is blown through the culture medium as the entire medium is agitated by stirring. The rate of aeration can be from about 0.1 to about 1.0 volume of air per volume of culture medium per minute. Preferably, the rate of aeration is at least 0.5 volume of air per volume of culture medium per minute.

Generally under the fermentation conditions described above, maximum production of factor G occurs within about 4 to 6 days. The course of the fermentation can be followed by assaying aliquots of the culture medium from time to time for antibiotic activity. One suitable assay organism is *Bacillus subtilis*. Activity vs. this organism is determined by a standard microbiological plate assay such as the cup-plate or paper-disc method on agar plates inoculated with the assay organism.

In the recovery of factor G from its fermentation broth, chromatography over a non-functional resin is preferred. The diaion HP 20 resin manufactured by Mitsubishi is a suitable non-functional resin. Other similar non-functional resins such as Amberlite XAD-4 (Rohm and Haas Co.) and Duolite SES 861 (Diamond Shamrock) can also be used. To illustrate the recovery and isolation of factor G, the broth is diluted with a water miscible organic solvent such as acetone, and the pH of the whole diluted fermentation broth is lowered to a pH of between about 1.5 and 2.0, and the acidified broth is filtered to separate the mycelium and other insolubles. A filter aid such as diatomaceous earth or other commercially available filter aid is desirably used to enhance the rate of filtration. Also, the insolubles can be separated by centrifugation. The pH of the filtered broth is then raised to a pH of about 3 to about 4 and the broth is evaporated to remove the organic solvent. The filtered broth is then passed over the non-functional resin, and the antibiotic eluted with an aqueous organic solvent mixture such as aqueous methanol, aqueous ethanol, or aqueous acetone. Usually, the organic solvent comprises about 20% to about 50% by volume of the solvent mixture. The eluate fractions containing the antibiotic are concentrated to a small volume, and the antibiotic precipitates in the free base form from the concentrate after the pH is adjusted to about pH 6.5 to pH 7.

Alternatively, following the fermentation, factor G can be recovered from the fermentation medium by conventional isolation procedures such as adsorption on a suitable ion exchange resin followed by chromatographic separation. Suitable resins include low cross-linked cation exchange resins such as Amberlite IR-116.

As noted above, A-4696 factor G is a basic substance containing two basic amino groups. Factor G forms acid addition salts with inorganic and organic acids. The salts of factor G are prepared by conventional procedures, for example, the dihydrochloride salt is prepared by stirring the free base with hydrochloric acid in aqueous methanol. The dihydrochloride salt precipitates from the solution and is filtered and dried. The sulfate salt can be prepared by adding sulfuric acid to a solution of factor G in aqueous methanol or aqueous ethanol.

Factor G and the pharmaceutically acceptable non-toxic acid addition salts thereof inhibit the growth of microorganisms pathogenic to man and animals. For example, the minimum inhibitory concentration, MIC, of factor G vs. *Streptococcus pneumoniae* was 0.5 μg/ml. Against *Streptococcus pyogenes* the MIC was 0.25 μg/ml and vs. *Staphylococcus aureus* the MIC of factor G was 1.0 μg/ml. The minimum inhibitory concentrations were determined by the agar dilution method.

Factor G demonstrates in vivo activity against the same microorganisms. For example, in the mouse protection test the following $ED_{50}$ values were observed following administration of the antibiotic to mice injected with the indicated pathogen.

| Organism | $ED_{50}$ (mg/kg × 2, sc.) |
|---|---|
| *Streptococcus pneumoniae* | 0.39 |
| *Streptococcus pyogenes* | 0.57 |
| *Staphylococcus aureus* | ~0.78 |

Factor G and the pharmaceutically acceptable salts thereof can be used to control infections in man and animals when administered parenterally in an effective non-toxic dose of between about 1.5 mg/kg. and about 100 mg/kg. of body weight. The dose regimen may be varied from a single daily dose to multiple doses per day. The duration of treatment and the dosage amounts may vary depending on such factors as the particular microorganism involved, the severity of the infection, and the general condition of the host.

The antibiotic can be formulated in suitable parenteral unit dosage forms such as in vials for i.m. injection or, alternatively, it may be administered by i.v. infusion as a solution in a suitable physiological fluid such as Ringer's solution, 5% dextrose, or physiological saline.

Factor G is also effective in promoting weight gain in chickens when administered in the chicken's feed or drinking water. Factor G when incorporated in chicken feed at a concentration of between about 2.5 ppm. and about 100 ppm. increased the weight gain of the chickens with improved feed efficiency relative to controls. For administration in drinking water a pharmaceutically acceptable salt form of factor G is preferably used. The dihydrochloride salt of A-4696G is a suitable salt form of the antibiotic for this mode of administration. The concentration of A-4696G or a salt thereof in the bird's drinking water is between about 1.5 mcg/ml. to about 50 mcg/ml. and preferably at about 10–20 mcg/ml. Accordingly, in another aspect of this invention, there is provided a method for promoting the growth of chickens which comprises administering to chickens a growth promoting amount of A-4696 factor G or a pharmaceutically acceptable salt thereof.

As described above, factor G can be administered by incorporation in the bird's diet or alternatively in the drinking water. The birds may be maintained on the A-4696G containing diet throughout growth to achieve the maximum weight gain.

The A-4696G can be incorporated in the conventional feed stuffs used for chickens. For such purpose the isolated and substantially pure A-4696G factor can be used to mix with the bird's diet. Alternatively, a highly economical and convenient form of factor G for use in the method is obtained by drying the whole fermentation broth to obtain factor G commingled with the mycelium produced in the fermentation. The dried mycelium-A-4696G composition can be assayed for factor G content and the appropriate amount of the composition incorporated into the chicken diet. The mycelium-factor G composition also adds nutrient value to the diet in the form of saccharides and amino acids which are present in the mycelium.

The A-4696G-mycelium also can be obtained by separating the mycelium from the broth and, after removing factor G from the broth as described herein, concentrating the column eluates containing factor G and mixing the concentrate with the separated mycelium before drying.

A-4696 factor G and the pharmaceutically acceptable non-toxic salts thereof are effective growth promoters for ruminant animals such as cows, goats and sheep. The efficiency of carbohydrate utilization in ruminants is increased when the rumen flora is stimulated to produce propionate compounds rather than acetate or butyrate compound components of the rumen's volatile fatty acids (see Church et al., "Digestive Physiology and Nutrition of Ruminants", Vol. 2, 1971, pp. 622 and 625). A-4696G as the free base or preferably as a pharmaceutically acceptable salt enhances the production of propionates relative to acetates and butyrates in rumen fluid. For example, in tests carried out with rumen fluid in continuous fermentation flasks which mimic the action of the rumen, A-4696G enhances the production of propionates relative to the other fatty acids. The tests were carried out in the following manner.

The flasks used in the test were gas-tight flasks equipped with inlet ports for liquids and solids and gas outlet tubes connected to bladders for collection of the fermentation gases. The liquid volume of the test fluid in the flasks was maintained at 500 ml. by means of a stand pipe leading to a collection vessel. The contents of the flasks were stirred continuously during the test with a magnetic stirrer. During the test the temperature of the flasks was maintained at about 38° C. to about 40° C.

Into each flask were added 500 ml. of strained rumen fluid obtained from a fistulated steer, which was fed the same diet employed in the test fluid. The flasks were sealed and the gas collection bladders attached. Liquid buffer (pH 6.8-7.0) of the following composition was continuously added to the flask at a rate of about a liter per day.

| Ingredient | g./liter |
| --- | --- |
| Sodium hydrogen phosphate | 2.2 |
| Magnesium chloride | 0.036 |
| Sodium bicarbonate | 5.9 |
| Potassium chloride | 0.34 |
| Sodium chloride | 0.28 |
| Urea | 1.0 |
| Calcium chloride | 0.024 |

A 10 g. addition of feed was added twice daily to each flask. After each feeding, the gas outlet was closed and the flask flushed with carbon dioxide. The feed composition was 50% alfalfa hay and 50% of the following composition.

| Ingredient | Percent by Weight |
| --- | --- |
| Coarse ground corn | 40.85 |
| Ground corn cobs | 35 |
| Soybean meal (50% protein) | 8.1 |
| Alfalfa meal | 4 |
| Molasses | 10 |
| Urea | 0.65 |
| Dicalcium phosphate | 0.6 |
| Calcium carbonate | 0.3 |
| Sodium chloride | 0.3 |
| Vitamin A and $D_2$ premix | 0.07 |
| Vitamin E premix | 0.05 |
| Trace mineral premix | 0.04 |

The steer used to supply the rumen fluid was also maintained on the same feed.

Each day during the test the effluent liquid and gas were collected and analyzed. The fermentation was carried out for 4 days before the antibiotic was added to the feed. After the 4-day period of equilibration and when the composition of the effluent gas and liquid was relatively constant, the addition of the A-4696G containing feed was started and the fermentation continued for 7 days with the treated feed.

Acetate, propionate, and butyrate composition of the effluent liquid from each flask was determined by gas chromatography. The data obtained for A-4696G are shown in the following Table 5.

TABLE 5

| | | Effect of A-4696G On Rumen Composition | | | | |
| --- | --- | --- | --- | --- | --- | --- |
| | | VFA Production[2] | | | | |
| Treatment | Dosage[1] mcg/ml | $C_2$ | $C_3$ | $C_4$ | Total/ VFA | Molar Percent $C_3$ Production |
| Control | 0 | 43.6 | 15.2 | 5.4 | 64.2 | 23.7 |
| A-4696G[3] | 4 | 39.0 | 21.4 | 3.3 | 63.7 | 33.6 |

[1]Concentration in test solution
[2]Values listed are millimoles per day of volatile fatty acids (VFA)
[3]A-4696G free base An important aspect of this invention is a method of increasing the efficiency of feed utilization by ruminant animals having a developed rumen function, which comprises orally administering to such animals a propionate-increasing amount of A-4696G.

The method of this invention is practiced by orally administering at least the amount of A-4696G to increase the production of propionates in the rumen. The amount of A-4696G administered is from about 0.1 mg./kg. of body weight per day to about 5 mg./kg. per day. The preferred range of administration is between about 0.25 mg./kg./day and about 3 mg./kg./day.

The A-4696 factor G and the pharmaceutically acceptable salts thereof, for example, the sulfate, hydrochloride or phosphate salt, can be administered in the form of a sustained release bolus, or incorporated in a mineral or protein block, or in a feed supplement, or in the animal's whole feed. For animals on pasture, the administration via a sustained release bolus is a suitable manner to practice the present invention. Such boluses can be prepared with polymers which allow the slow payout of A-4696G for several weeks. Boluses are made of sufficiently high density so that they remain in the animal's rumen and are not carried through the digestive tract. High density can be achieved by adding metal particles to the bolus.

Mineral blocks containing A-4696G are also an advantageous method of administration to animals on pasture. Mineral blocks are old to animal husbandry and contain in highly compressed form physiologically suitable salts, minerals and nutrient materials such as phosphates, carbonates, calcium salts, trace elements, for example, zinc, manganese and the like, vitamins, steroids and other ingredients. A-4696G can be incorporated in such blocks in a concentration of from about 0.05% to about 5%.

The preferred manner of administering A-4696G is as an additive to the animal's feed. Feed compositions containing A-4696G and the pharmaceutically acceptable salts thereof are new compositions and, accordingly, are a further aspect of the present invention.

Animal feed compositions are usually prepared stagewise. First, the compound is mixed with inert ingredients to prepare a feed premix, which is the form in which the compound is shipped from the original manufacturer to a local feed mill. Premixes may be either liquid or solid, and may contain from about 1% to about 90% of the compound. The inert ingredients of a feed premix are not critical, and may be any of the conventionally-used physiologically-acceptable carriers. Liquid carriers include, for example, glycols such as polyethylene glycols of various molecular weights and propylene glycol, inert oils including vegetable oils and refined mineral oil, and physiologically-acceptable alcohols such as ethanol. Solid premix carriers include, for example, vermiculite, diatomaceous earth, physiologically-acceptable clays such as attapulgite and montmorillonite, and granulated or powdered feed components such as cracked corn, soybean meal, alfalfa meal, rice hulls, crushed corncobs, cracked wheat or oats and all sorts of waste materials of grain processing. Such ingredients of solid feed premixes are often granulated, pelleted or otherwise treated to assure that the feed premix remains homogeneous.

The following are typical examples of feed premix compositions which are embodiments of the present invention.

| I. | |
|---|---|
| Ground oats | 84% |
| Propylene glycol | 2 |
| Lignin | 3 |
| A-4696G dihydrochloride | 11 |
| II. | |
| Yellow corn | 24% |
| Ground corn cobs | 25 |
| Mineral oil | 1 |
| A-4696G sulfate | 50 |
| III. | |
| Soybean meal | 10% |
| A-4696G phosphate | 90 |
| IV. | |
| Polyethylene glycol | 90% |
| A-4696G dihydrochloride | 9 |
| Polyoxyethylene ester | 1 |
| V. | |
| Vermiculite | 33% |
| Cottonseed oil | 2 |
| A-4696G | 65 |
| VI. | |
| Rice hulls | 22.5% |
| Molasses | 2.5 |
| A-4696G sulfate | 75 |
| VII. | |
| Mineral oil | 90% |
| Polyglycerol ester | 5 |
| A-4696G | 5 |
| VIII. | |
| Ground corn cobs | 74% |
| Soybean oil | 1 |

-continued

| | |
|---|---|
| A-4696G dihydrochloride | 25 |

Preferred premix compositions are those containing about 50 g. of A-4696G or a salt thereof per pound of premix or 100 g. of A-4696G or salt form thereof per pound of premix.

A second stage in the manufacture of animal feeds is the feed supplement or concentrate. Such supplements are compositions containing a compound of this invention, mixed with nutritive substances such as minerals, inorganic salts, trace elements and vitamins. Supplements are often mixed by diluting a feed premix with other constituents, and are often made up by local feed mills for use by large livestock operations. A supplement may be used in the manufacture of complete mixed feed compositions containing A-4696G or may be simply poured over unmedicated feed in the feed troughs or feed bunkers. The concentration of A-4696G in supplements varies widely, depending on the amount of the supplement to be fed to each animal. In general, concentrations are from about 0.01% to about 1%, preferably from about 0.02% to about 0.5%. Examples of feed supplement compositions containing compounds of this invention are the following:

| I. | |
|---|---|
| Ground corn cobs | 38.5% |
| Soybean meal | 25.0 |
| Ground corn | 20.0 |
| Ground oats | 10.0 |
| Molasses | 2.5 |
| Salt | 0.4 |
| Vitamin premix | 1.1 |
| Animal fat | 1.5 |
| A-4696G phosphate | 1.0 |
| II. | |
| Soybean meal | 64.29% |
| Biuret | 10.0 |
| Dicalcium phosphate | 4.2 |
| Sodium tripolyphosphate | 2.1 |
| Sulfur | 0.4 |
| Molasses | 6.0 |
| Salt | 12.8 |
| Trace mineral premix | 0.2 |
| A-4696G | 0.01 |
| III. | |
| Soybean meal | 49.59% |
| Alfalfa meal | 24.8 |
| Urea | 12.4 |
| Dicalcium phosphate | 2.5 |
| Ground limestone | 7.4 |
| Salt | 2.5 |
| Vitamin premix | 0.8 |
| A-4696G sulfate | 0.01 |
| IV. | |
| Soybean meal | 89.55% |
| Dicalcium phosphate | 10.0 |
| A-4696G dihydrochloride | 0.45 |
| V. | |
| Soybean meal | 10.75% |
| Urea | 20.0 |
| Dicalcium phosphate | 16.0 |
| Calcium carbonate | 24.0 |
| Salt | 20.0 |
| Sodium bicarbonate | 2.0 |
| Trace mineral and vitamin premix | 7.2 |
| A-4696G | 0.05 |

Feeds for ruminant animals are usually and preferably cereal-based, adapted to the needs of such animals. The usual dry or slurried ruminant feeds, based on grains such as wheat, oats, barley, corn and the like, are treated with the compounds of this invention just as animal feeds have long been routinely treated with medicaments in the practice of the animal husbandry art. Such feeds routinely are composed of the basic grains, and are further supplemented with vitamins, minerals, inorganic salts and other important nutritive substances to assure that the ruminant animals are properly nourished. Feed should contain from about 5 parts per million (ppm.) to about 500 ppm. of A-4696G or a salt thereof; preferable feeds should contain from about 10 ppm. to about 250 ppm. For example, the following are typical feed compositions making use of compounds of this invention.

| I. | |
|---|---|
| Chopped alfalfa | 54.88% |
| Sorghum grain | 36.20 |
| Soybean meal | 4.10 |
| Urea/grain mixture, 70% protein | 3.60 |
| Dicalcium phosphate | 0.90 |
| Trace mineralized salt | 0.23 |
| Vitamin supplement | 0.09 |
| A-4696G | 5 ppm |
| II. | |
| Ground sorghum | 60.0% |
| Alfalfa meal | 15.0 |
| Cottonseed hulls | 15.0 |
| Cottonseed meal | 8.5 |
| Salt | 1.0 |
| Ground limestone | 0.5 |
| A-4696G phosphate | 250 ppm |
| III. | |
| Wheat | 44.54% |
| Corn cobs | 45.00 |
| Cane molasses | 3.00 |
| Soybean meal | 6.40 |
| Dicalcium phosphate | 0.65 |
| Limestone | 0.38 |
| Trace minerals | 0.03 |
| A-4696G | 50 ppm |
| IV. | |
| Ground timothy hay | 15% |
| Ground alfalfa hay | 15 |
| Cracked corn | 50 |
| Soybean oil meal | 10 |
| Molasses | 9 |
| Trace mineralized salt and vitamin premix | 1 |
| A-4696G sulfate | 100 ppm |

The A-4696 factor G is also useful as a growth promotant for poultry and swine. For this purpose, A-4696G and the pharmaceutically acceptable salts thereof are administered in the animal's feed or drinking water. Preferably, the dihydrochloride salt of A-4696G or other water soluble salt form is administered in drinking water.

The following Examples further illustrate the present invention.

EXAMPLE 1

Preparation of A-4696G

A nutrient agar slant having the following composition was prepared for inoculation with the A-4696G producing strain.

| Ingredient | Amount (% by weight) |
|---|---|
| Cerelose | 0.5 |
| Potato dextrin | 2.0 |
| Nutrisoy flour | 1.5 |

| Ingredient | Amount (% by weight) |
|---|---|
| Yeast extract | 0.25 |
| Calcium carbonate | 0.1 |
| Agar | 2.0 |

The slant was inoculated with A-4696G ATCC 31681 and then incubated at 30° C. for about 6 days. After incubation the mycelial mat on the slant culture was covered with sterile distilled water and scraped loose with a sterile rod or loop to obtain an aqueous suspension of the mycelium.

The aqueous suspension was used as the inoculum for 100 ml. of sterile vegetative medium having the same composition as the agar slant medium described above. The inoculated medium was incubated for about 48 hours at a temperature of about 30° C. During incubation the vegetative medium was agitated on a rotary shaker operating at about 250 rpm. Following the growth of the vegetative medium, 10 ml. of the grown culture was withdrawn and used as the inoculum for sterile bump medium having the following composition.

| Ingredient | Amount (% by weight) |
|---|---|
| Cerelose | 0.5 |
| Yeast | 0.25 |
| Nutrisoy flour | 1.5 |
| Corn starch | 2.0 |
| Calcium carbonate | 0.1 |
| Antifoam agent (Sag 471)* | 0.05 |

*Sag 471 - silicone antifoam agent available from Union Carbide.

The bump medium was incubated for about 24 hours at a temperature of about 30° C. while agitated on a rotary shaker at 250 rpm. The grown bump medium was then used to inoculate the A-4696G sterile production medium of the following composition.

| Ingredient | Amount (% by weight) |
|---|---|
| Cerelose | 2.5 |
| Yeast | 2.0 |
| Calcium carbonate | 0.2 |
| Ammonium sulfate | 0.025 |
| Dipotassium acid phosphate | 0.05 |
| Glycerine | 1.5 |
| Molasses | 1.5 |
| Corn starch | 3.5 |
| Antifoam agent (Sag 471) | 0.03 |

The fermentation was carried out for 143 hours at a temperature of about 30° C. With stirring and aeration with sterile air at a rate of about one-half volume of air per volume of culture medium per minute. During the fermentation the pH of the medium increased from an initial pH of about 6.5 to a pH of about 8.0.

A portion (30 liters) of the whole fermentation broth was diluted with 30 liters of acetone and the pH adjusted to 1.8 with 6N hydrochloric acid. The acidified whole broth was filtered using a filter aid and the insolubles were washed with water on the filter. The pH of the filtrate was adjusted to 3.5 with 150 ml. of 50% sodium hydroxide and the filtrate concentrated in vacuo to a volume of 29 ml. The pH was readjusted from 2.2 to 3.1 with sodium hydroxide and refiltered to remove insolubles. The filtrate containing the antibiotic was passed over a 3-inch diameter column containing 5 liters of Mitsubishi Dianion HP-20 non-functional resin (styrene-divinylbenzene resin) pre-treated with methyl alcohol and washed with water. The flow rate was 250 ml/min. After adsorption of the antibiotic on the resin, the column was washed with 5 liters of water and eluted successively with 21 liters of 20% aqueous methyl alcohol, 15 liters of 50% aqueous methyl alcohol, and 15 liters of 50% aqueous acetone. Four-liter fractions of wash and eluate were collected. Fractions 8, 9 and 10 contained the majority of the antibiotic activity and were also free from most of the impurities. Fractions 8, 9 and 10 were combined and concentrated to a volume of 6 liters under vacuum. After the pH of the concentrate was adjusted to pH 6.8 with aqueous sodium hydroxide, the concentrate was poured into 60 liters of isopropyl alcohol. A-4696G precipitated from this mixture and was filtered and dried. There were obtained 54.2 g. of A-4696G in substantially pure form.

EXAMPLE 2

Preparation of A-4696G Dihydrochloride Salt

A-4696G free base is dissolved in aqueous methanol, and the solution is diluted with 1N hydrochloric acid. After stirring, the acidified solution may be diluted with acetone to precipitate the A-4696G dihydrochloride salt.

EXAMPLE 3

Alternate Preparation of A-4696G

Fermentation broth prepared according to the procedure of Example 1 was filtered after the addition of 5% (wt/vol) filter aid (Celite 545). The filter cake was resuspended in an equal volume of deionized water and the pH of the aqueous suspension was adjusted to pH 10.5 with aqueous sodium hydroxide. The suspended solids were separated by filtration and washed with water. The filtrate and the washings were combined, and the resulting solution was acidified with 20% (wt/vol) aqueous sulfuric acid to pH 4.5. The acidic solution was clarified by filtration using 1% filter aid (Celite 545). The clear solution was passed through a column containing Amberlite IR-116 (Na+ form), and the column was washed with deionized water. The IR-116 resin was removed from the column and eluted batchwise at pH 10.5 with an aqueous solution of sodium hydroxide. The resin eluate was neutralized (pH 7) with 20% (wt/vol) aqueous sulfuric acid, then washed with three portions of deionized water. The water washes were neutralized and combined with the neutralized eluate. The resulting solution was concentrated and subsequently freeze dried.

The crude complex thus obtained was slowly added with vigorous stirring to deionized water. The resulting suspension was stirred for twenty minutes and was subsequently neutralized (pH 7) using a 10% aqueous ammonium hydroxide solution. To insoluble A-4696G was separated by vacuum filtration, washed with deionized water, and freeze dried.

The dried, desalted A-4696G thus obtained was suspended in deionized water, and the pH of the suspension was adjusted to pH 2.7 by addition of 3N aqueous hydrochloric acid. The acidified solution was centrifuged for 40 minutes at 2500 rpm. The supernatant was decanted and loaded on a column containing decolorizing resin (Duolite S761). The activity was eluted with deionized water at a flow rate of 30 ml/min. The elution was monitored by thin layer chromatography (TLC). The antibiotic A-4696G-containing effluent was concentrated (3 mm., 35° C.) and freeze dried.

The dried, decolorized antibiotic A-4696G thus obtained was dissolved in deionized water. The resulting aqueous solution was filtered and loaded on a chromatography column containing polyamide (Machery & Nagel SC6). The column was eluted with deionized water. The elution was monitored by UV-activity and by TLC. Fractions were combined according to TLC identity and freeze dried. Additional purification was achieved by repeated chromatography.

We claim:

1. The method of producing the antibiotic A4696G of the formula

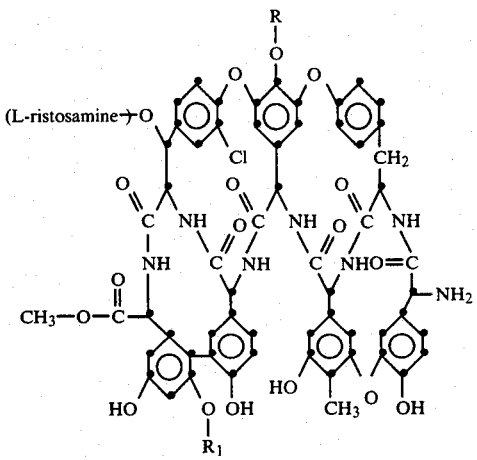

wherein R is

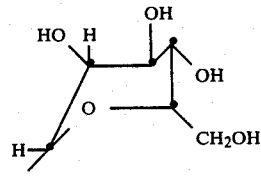

and $R_1$ is

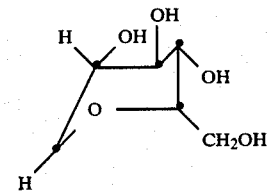

which comprises cultivating the organism *Actinoplanes missouriensis* ATCC 31681 in an aqueous nutrient culture medium containing assimilable sources of carbon, nitrogen, and inorganic salts under submerged aerobic fermentation conditions until a recoverable amount of antibiotic A4696G is produced by said organism in said culture medium.

2. A biologically pure culture of the microorganism, *Actinoplanes missouriensis* strain ATCC 31681, which on culturing in an aqueous nutrient medium is capable of producing antibiotic A-4696G.

* * * * *